United States Patent [19]
Beach et al.

[11] Patent Number: 5,183,046
[45] Date of Patent: Feb. 2, 1993

[54] ULTRASONIC PLETHYSMOGRAPH

[75] Inventors: Kirk W. Beach; David J. Phillips, both of Seattle, Wash.; John Kansky, Indianapolis, Ind.

[73] Assignee: Board of Regents of the University of Washington, Seattle, Wash.

[21] Appl. No.: 792,584

[22] Filed: Nov. 15, 1991

Related U.S. Application Data

[63] Continuation of Ser. No. 644,477, Jan. 18, 1991, Pat. No. 5,088,498, which is a continuation of Ser. No. 258,534, Oct. 17, 1988, abandoned.

[51] Int. Cl.$^5$ ................................................ A61B 8/08
[52] U.S. Cl. ................................................ 128/661.07
[58] Field of Search ........................ 128/661.07–661.10

[56] References Cited

U.S. PATENT DOCUMENTS

| | | | |
|---|---|---|---|
| 3,631,849 | 1/1972 | Norris | 128/661.08 |
| 4,122,427 | 10/1978 | Karsh | 128/661.07 |
| 4,370,985 | 2/1983 | Takeichi et al. | 128/661.1 X |
| 4,751,847 | 6/1988 | Katakura et al. | 128/661.09 X |
| 5,088,498 | 2/1992 | Beach et al. | 128/661.07 |

OTHER PUBLICATIONS

Maulik, D. et al., "Fetal Doppler Echocardiography: . . . Abnormal Hemodynamics" Feb. 1, 1984, vol. 53, pp. 572–578.

Kay, L. et al, "The echocardiophone: a new means for observing spatial movement of the heart", *Ultrasonics*, vol. 15, No. 3, May 1977.

Seeds, J. W. et al, *Practical Obstetrical Ultrasound*, Aspen Publications, Rockville, Md., 1986, pp. 124–129.

"Vascular Ultrasound Ultrasonic Evaluation of the Carotid Bifurcation", by Langlois, Roederer and Strandness, published in vol. 4, No. 2, of *Echocardiography A Review of Cardiovascular Ultrasound* (Futura Publishing Company, Inc., 1987).

*Doppler Ultrasound and its Use in Clinical Measurement*, Peter Atkinson and John P. Woodcock, (San Francisco: Academic Press, 1982), particularly pp. 54 to 74.

*Biomedical Ultrasonics*, P. N. T. Wells, (San Francisco: Academic Press, 1977), particularly Chapter 9.

"Doppler Ultrasound: A technique for Obtaining Arterial Wall Motion Parameters," *IEEE Transactions*, Charles F. Olsen.

"On the Development of a Multigate Pulsed Doppler System With Serial Data Processing", A. P. G. Hoeks, Ph.D. Thesis University of Limburg, Maastricht, Holland, 1982.

"Doppler Measurement of Myocardial Thickening With a Single Epicardial Transducer," *American Journal of Physiology*, Craig J. Hartley et al., 245: 6 (1983), pp. H1066–H1072.

"Ultrasonic Measurement of Small Displacements and Deformations of Tissue," *Ultrasonic Imaging*, L. S. Wilson and D. E. Robinson, 4 (1982), pp. 71 to 82.

*Primary Examiner*—Francis Jaworski
*Attorney, Agent, or Firm*—Christensen, O'Connor, Johnson & Kindness

[57] ABSTRACT

Quadrature phase signals (I and Q) from a pulsed Doppler medical instrument are analyzed to detect phase changes of consecutive echoes from tissue at a depth of interest. Such phase changes are analyzed to determine tissue displacement. Relative displacements at different depths are examined to detect tissue expansion and contraction. The area of the uterus of a pregnant female can be scanned and the frequency of tissue displacement or expansion and contraction examined to determine pulsations due to blood supplied by the fetal heart and/or pulsations due to blood supplied by the maternal heart. Conventional M-mode or B-mode images can be colorized differently for different frequencies of tissue displacement.

14 Claims, 5 Drawing Sheets

| IN LL ARRAY | IN TL ARRAY | MEANING |
|---|---|---|
| 00 | 00 | NO DISPLACEMENT |
| 00 | 01 | 40 $\mu$ TOWARDS THE TRANSDUCER |
| 00 | 10 | 40 $\mu$ AWAY FROM THE TRANSDUCER |
| 00 | 11 | ALIASED DATA* |
| 01 | 00 | 40 $\mu$ AWAY FROM THE TRANSDUCER |
| 01 | 01 | NO DISPLACEMENT |
| 01 | 10 | ALIASED DATA* |
| 01 | 11 | 40 $\mu$ TOWARDS THE TRANSDUCER |
| 10 | 00 | 40 $\mu$ TOWARDS THE TRANSDUCER |
| 10 | 01 | ALIASED DATA* |
| 10 | 10 | NO DISPLACEMENT |
| 10 | 11 | 40 $\mu$ AWAY FROM TRANSDUCER |
| 11 | 00 | ALIASED DATA* |
| 11 | 01 | 40 $\mu$ AWAY FROM THE TRANSDUCER |
| 11 | 10 | 40 $\mu$ TOWARDS THE TRANSDUCER |
| 11 | 11 | NO DISPLACEMENT |

*Fig. 8*

ULTRASONIC PLETHYSMOGRAPH

This application is a continuation of our copending U.S. application Ser. No. 07/644,477, filed Jan. 18, 1991, for Ultrasonic Plethysmograph, now U.S. Pat. No. 5,089,498 of U.S. Pat. application Ser. No. 07/258,534, filed Oct. 17, 1988, now abandoned.

BACKGROUND OF THE INVENTION

1. Field of the Invention

The present invention relates to noninvasive diagnostic medical devices utilizing ultrasound.

2. Prior Art

In ultrasonic medical devices, ultrasound is beamed into the body by a transmitting transducer and waves reflected from internal matter are detected by the same or a separate receiving transducer.

A first category of ultrasonic medical devices is the Doppler device which detects the difference in frequency of reflected waves as compared to the frequency of reflected waves as compared to the frequency of the transmitted waves. The difference in frequency of a wave before and after its reflection indicates the velocity of the matter from which the wave was reflected. Doppler devices are often used for analyzing blood flow through an artery, for example.

In a continuous wave (CW) Doppler device, the ultrasound is continuously transmitted into the body and the reflected waves are continuously monitored for Doppler shift. Separate transmitting and receiving transducers are required and it is not possible to differentiate between waves reflected at different distances from the transmitting transducer.

In a pulsed Doppler device, short bursts of ultrasound are transmitted at uniform intervals. Reflected waves from a desired depth can be monitored by analyzing the received ultrasound signal the appropriate length of time after a pulse or burst of ultrasound was transmitted. Such a system is referred to as a "range-gated" system. The "range gate" is the short period following the transmission during which the received wave form is monitored. In sophisticated systems, there can be several range gates so that the reflected wave form is monitored for each of several different short periods following the pulse transmission, corresponding to the reflection of transmitted waves at each of several different depths. FIG. 1 illustrates the transmitted pulse of ultrasound, the echo and the range gate spaced a predetermined period of time $t_d$ from the beginning of the transmitted pulse. During the range gate period the echo is sampled or monitored to detect the portion reflected from a desired depth.

In one type of medical Doppler device, the electrical signal representing the reflected wave is demodulated to produce an audio-frequency signal varying in frequency (pitch) depending on the difference in detected velocity (Doppler shift). The demodulated signal is fed to a speaker and the resulting sound is indicative of blood flow, such as pulsing of blood through an artery. An example of such a device is the Versadopp TM 10 device available from Diagnostic Ultrasound Corporation of Kirkland, Washington.

In other medical Doppler devices, the signal representing the reflected wave is fed to a frequency spectrum analyzer which can actuate a video display. Such a display can show a curve representing amplitude on the vertical axis and frequency on the horizontal axis. For analyzing blood flow, the relative amplitude of each frequency component indicates the proportion of blood flowing at the corresponding velocity. Another type of display indicates frequency on the vertical axis and time on the horizontal axis with amplitude represented by brightness. See, for example, the article titled "VASCULAR ULTRASOUND Ultrasonic Evaluation of the Carotid Bifurcation", by Langlois, Roederer and Strandness, published in Vol. 4, No. 2, of *ECHOCARDIOGRAPHY A Review of Cardiovascular Ultrasound* (Futura Publishing Company, Inc., 1987).

Medical Doppler devices provide information on the velocity of the matter from which the ultrasound is reflected relative to the transmitting transducer. Information on the direction, i.e., toward or away from the transducer, can be obtained by utilizing "quadrature phase signals" generated by known devices as represented in FIG. 2. As pertinent to the present invention, the received signal is compared with two reference signals that are identical except that one signal is 90 degrees out of phase relative to the other signal. Separate demodulators produce outputs commonly known as "I" and "Q" which also are 90 degrees out of phase. Velocity information can be calculated from a single signal and velocity and relative direction can be detected from the two signals. See Peter Atkinson and John P. Woodcock, *Doppler Ultrasound and its Use in Clinical Measurement*, (San Francisco: Academic Press, 1982), particularly pages 54 to 74.

Another type of noninvasive ultrasonic medical diagnostic device is the "imaging" ultrasound device. Ultrasonic imaging systems are concerned with the amplitude of the reflected wave as a function of time. The amplitude and time information indicate the location of interfaces between different types of tissue having different impedances to ultrasound waves. In a "motion mode" (M mode) system, range gating is utilized to detect amplitude at different depths which can be represented as the vertical axis on a video display. Brightness indicates amplitude and the horizontal axis represents time so that motion of internal tissue along approximately the line of transmission and reflection is indicated on the display.

In a brightness mode (B mode) imaging system, echoes are monitored along closely adjacent transmission axes such as by sweeping the pulsed transmitting-receiving transducer. The desired result is a two-dimensional cross-sectional image of internal structure such as a tumour or a fetus. See P. N. T. Wells, *Biomedical Ultrasonics*, (San Francisco: Academic Press, 1977), particularly Chapter 9.

Another pertinent type of medical diagnostic device is the plethysmograph designed to measure expansion and contraction of tissue caused by pulsation of blood through the tissue. Some such devices utilize a fluid-filled cuff encircling a limb and measuring displacement of fluid in the cuff (water-filled) or change in pressure (air-filled). Other such devices measure change in tissue electrical impedance or stretching of tissue (strain gauge) or change in optical properties of the tissue being examined (fluctuations in translucency).

There have been attempts to measure displacement of internal matter by use of medical ultrasound devices, primarily movement of arterial walls, such as described in: Charles F. Olsen, "Doppler Ultrasound: A Technique for Obtaining Arterial Wall Motion Parameters," *IEEE Transactions;* A. P. G. Hoeks, "On the Development of a Multigate Pulsed Doppler System With Serial Data Processing." Ph.D Thesis University of Limburg, Maastricht, Holland, 1982; and Craig J. Hartley et. al., "Doppler Measurement of Myocardial Thickening With a Single Epicardial Transducer," *American Journal of Physiology*, 245: 6 (1983), pages H1066-H1072. In general, Doppler techniques are utilized to determine tissue velocity. Velocity as a function of time indicates distance or displacement. An accurate measurement is difficult because of the errors introduced during detection of frequency and the mathematical frequency analysis. More pertinent to the present invention is the system described in L. S. Wilson and D. E. Robinson, "Ultrasonic Measurement of Small Displacements and Deformations of Tissue," *Ultrasonic Imaging*, 4 (1982), pages 71 to 82, because in that system there is an attempt to monitor the phase of the reflected ultrasound. to the devices measuring frequency shift, the phase signal is analyzed mathematically by integration to approximate displacement of tissue. Consequently, errors can be introduced both in phase measurement and.

SUMMARY OF THE INVENTION

The present invention provides an ultrasonic medical diagnostic device capable of analyzing quadrature phase signals I and Q in a pulsed transmission range gated system to measure the phase change of the echo at different depths. The phase information is analyzed over time to determine directly displacement of the tissue that reflected the ultrasound. The phase information can be converted to binary numbers for storage in the memory of and analysis by a computer. The diagnostic device quantifies the displacement of tissue at different depths and compares the displacement at difference depths for quantifying the relative expansion and contraction of tissue caused by blood passing through it. An output signal can indicate frequency and/or amplitude of tissue expansion and contraction.

BRIEF DESCRIPTION OF THE DRAWINGS

FIG. 8 is a chart showing two-bit binary representations of change in phase of returning echoes and indicating the significance of the phase changes or transitions.

DETAILED DESCRIPTION

Figure 1:
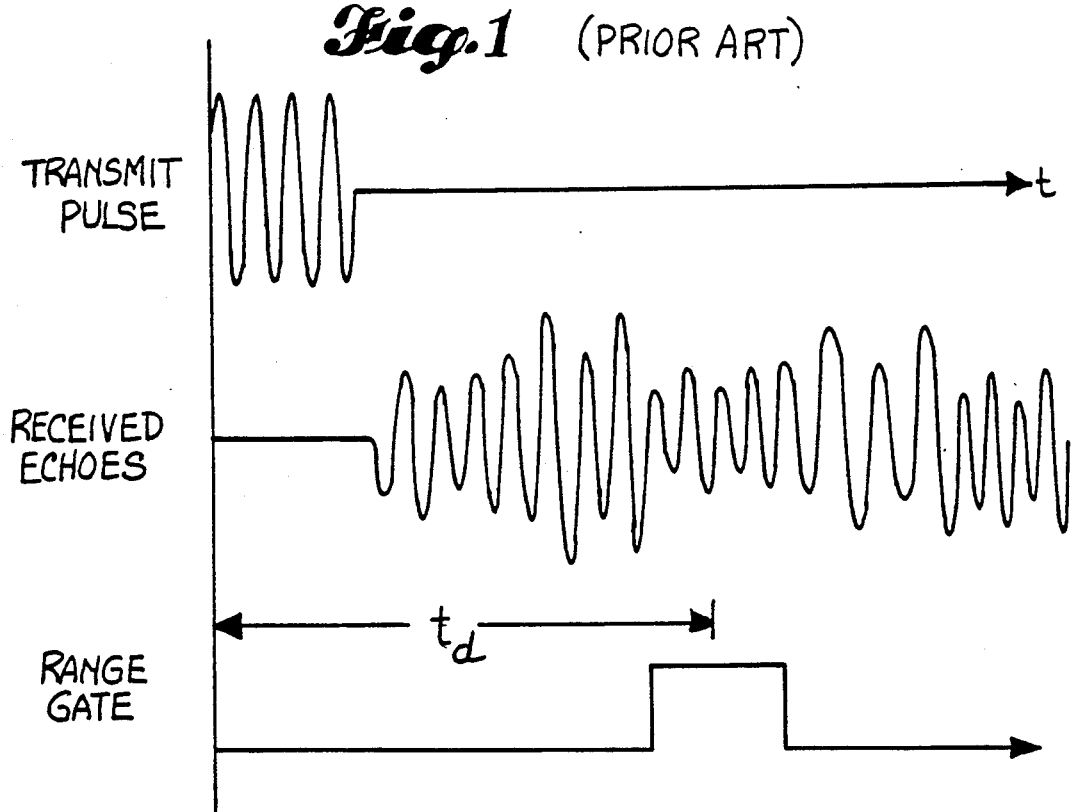
FIG. 1 is a diagrammatic representation of a pulse of ultrasound transmitted into a patient's body by an ultrasonic by internal body matter toward such device and the time interval for sampling echo to determine the signal reflected from a particular depth of interest.
Figure 2:
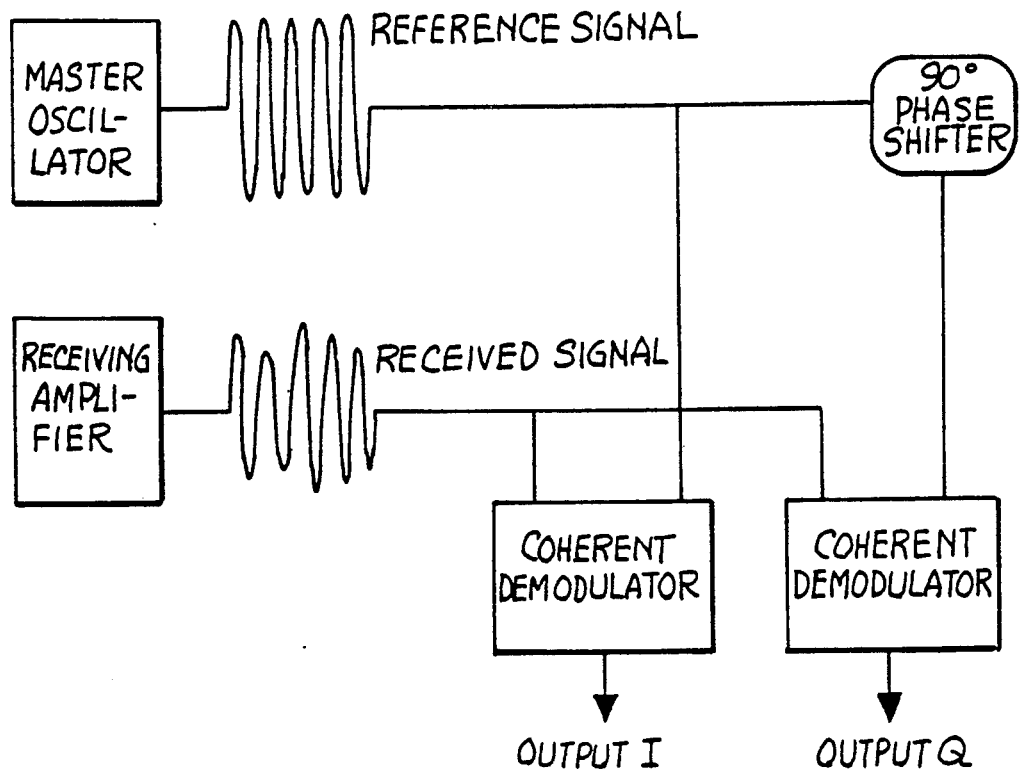
FIG. 2 is a schematic block circuit diagram of components of a known ultrasound Doppler device.
Figure 3:
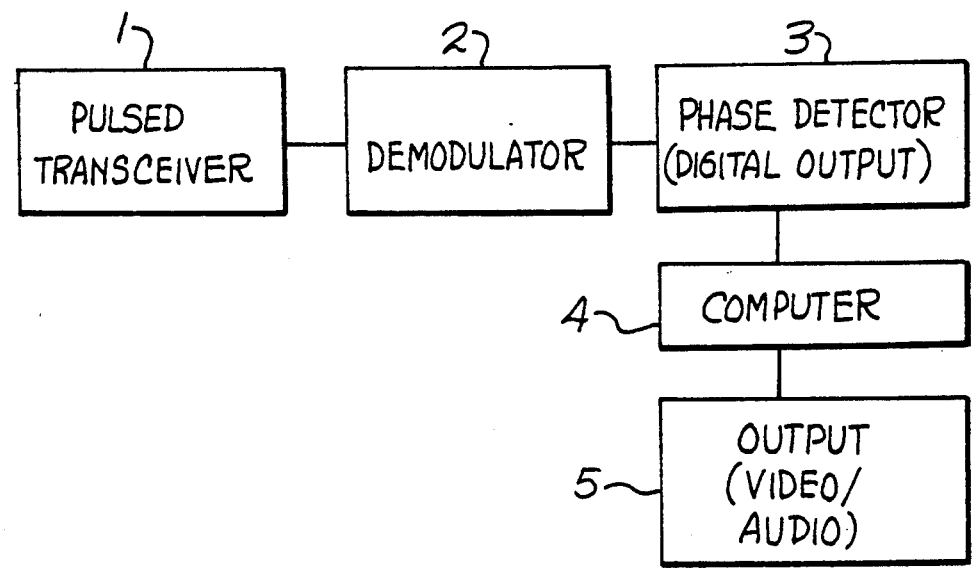
FIG. 3 is a block circuit diagram of an ultrasonic medical diagnostic device in accordance with the present invention.

With reference to FIG. 3, the medical ultrasound device in accordance with the present invention utilizes a conventional pulsed transceiver 1 for transmitting bursts of ultrasound into the body. The transceiver also detects reflected ultrasound and converts the reflected signal into a corresponding electrical signal. Such electrical signal is fed to a conventional demodulator component 2. The demodulator component preferably provides the standard "I" and "Q" signals. In accordance with the present invention, the demodulated signal is fed to a phase detector 3 which, for each transmitted pulse, determines the phase of the returning echo at each of several range gates, i.e., the phases for ultrasound reflected at each of several different depths. As discussed in more detail below, the difference in phase from one pulse to the next can provide a very precise indication of the distance traveled by the reflective tissue. Phase detector 3 provides a digital output indicative of the phases of the monitored reflected signals from different depths and feeds the digital information to a computer 4 for storage in memory and analysis prior to actuation of an output unit 5. In some cases the output unit will generate an audio output and in other cases the output unit will generate a video output.

In one embodiment, the quadrature signals I and Q are obtained by use of a model 400B pulsed Doppler unit available from Advanced Technology Laboratories. In such unit, the I and Q signals are normally fed to a sample and hold gate and filtered to give the familiar audio output associated with Doppler. For use in the present invention, the I and Q signals are obtained prior to such sample and hold gate. The transmission frequency of such unit is 5 megahertz and the pulse repetition frequency can be modified to be an integral multiple of 480 hertz up to 3.85 kilohertz depending on the time interval between pulses required to extract information from the maximum depth of interest. Each pulse can consist of approximately five cycles. Following each transmit pulse, the returning echo can be sampled up to sixty-four times at intervals of 1.6 microseconds. Assuming a speed of ultrasound through body tissue of 154,000 centimeters per second, the 1.6 microseconds time interval between samples corresponds to sampling reflections occurring about every 1.25 millimeters from the face of the transducer up to a maximum depth of about 8 centimeters. In the representative embodiment, phase shifts of plus or minus 90 degrees are measured from sample to sample. For the 5 megahertz transmission frequency, a 90-degree change in phase corresponds to movement of the tissue reflecting the ultrasound of about 40 micrometers toward or away from the transducer. Consequently, unless the reflecting tissue is displaced more than 40 micrometers in the time interval between consecutive pulses, the digital output from the phase detector provided a heretofore unattainably precise measurement of the displacement of tissue at each of several closely spaced depths.

More specifically, in the representative embodiment and I and Q signals from the model 400B ATL unit have a 6-volt DC offset. Minus 6 volts is introduced to remove the DC component. The remaining AC quadrature signals I and Q are sampled simultaneously but independently and the sign (positive or negative) of each signal is detected. If the voltage is positive, that signal is assigned a value of "1" and if the voltage is negative the signal is assigned a value of "0". There are four possible combinations for the I and Q signals as represented in FIGS. 4 through 7. The diagrams at the left indicate the phase quadrant of the two signals at the time of sampling. The graphs at the right represent the corresponding positions of the signals at the time of sampling which is indicated by the arrows.

Figure 4:
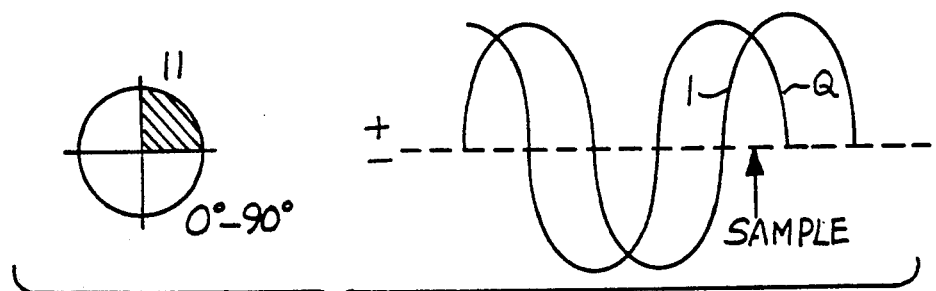
FIGS. 4, 5, 6 and 7 are corresponding diagrams and graphs of signals of the type analyzed by use of the ultrasonic medical device in accordance with the present invention to obtain information on the phase of ultrasound echoes.

Referring to FIG. 4, during the "first" 90 degrees, both I and Q are positive. Q is arbitrarily assigned as the right digit of a two-bit binary number and I as the left digit. The FIG. 4 relationship is characterized as "11".

Figure 5:
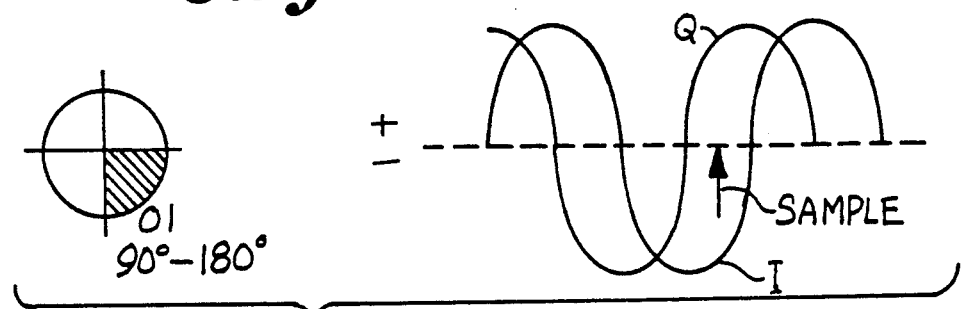

Referring to FIG. 5, during the next 90 degrees of phase (90 degrees to 180 degrees), signal Q will be positive but signal I is negative so tat the relationship is "01".

Figure 6:
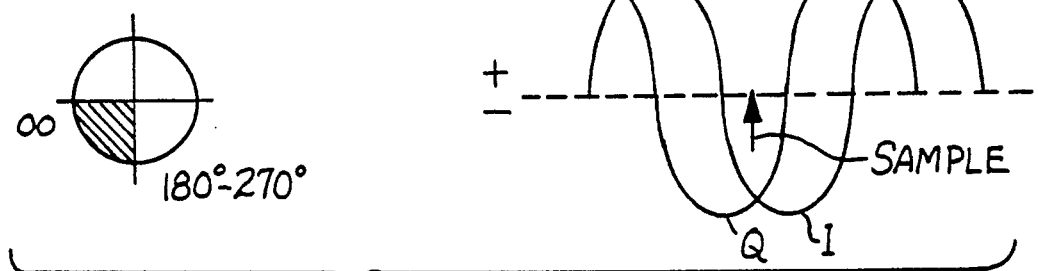

With reference to FIG. 6, during the next 90 degrees of phase (180 degrees to 270 degrees), both signals are negative and the relationship is assigned the binary number "00".

Figure 7:
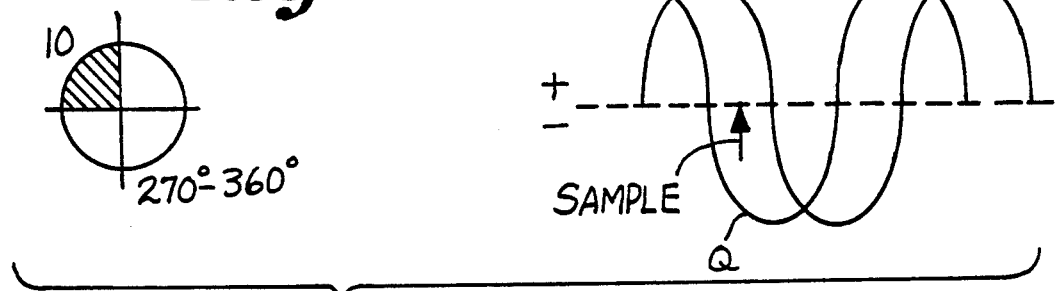

Finally, as represented in FIG. 7, during the next 90 degrees of phase (270 degrees to 360 degrees) signal I is positive and signal Q is negative and the relationship is assigned the value "10".

At each sampling, the appropriate two-digit binary number is stored in computer memory. In order to conserve memory space, such number can be stored as two bits of a longer number having other two-bit combinations representing the sampling at different depths.

At the end of the appropriate period, a new pulse is transmitted and a second sampling is taken for each of the discrete depths. The previous sampling is referred to as "last line" (LL) and the current sampling is referred to as "this line" (TL). FIG. 8 illustrates the possible changes from "last line" to "this line" and their significance. For example, if the previous sampling for tissue at a given depth was "00" and the new sampling indicates the same value, no displacement has occurred, whereas if the new value is 01, there has been displacement of 40 micrometers toward the transducer. If the "this line" value has changed to 10, there has been 40 micrometers displacement away from the transducer. It will be seen that there are four possible transitions (00 to 11, 01 to 10, 10 to 01, 11 to 00) which are ambiguous. Those transitions are characterized as "aliased data" and ignored. In practice, however, aliased data rarely occurs because of the precision of the unit and the fast pulse repetition frequency.

Figure 9:
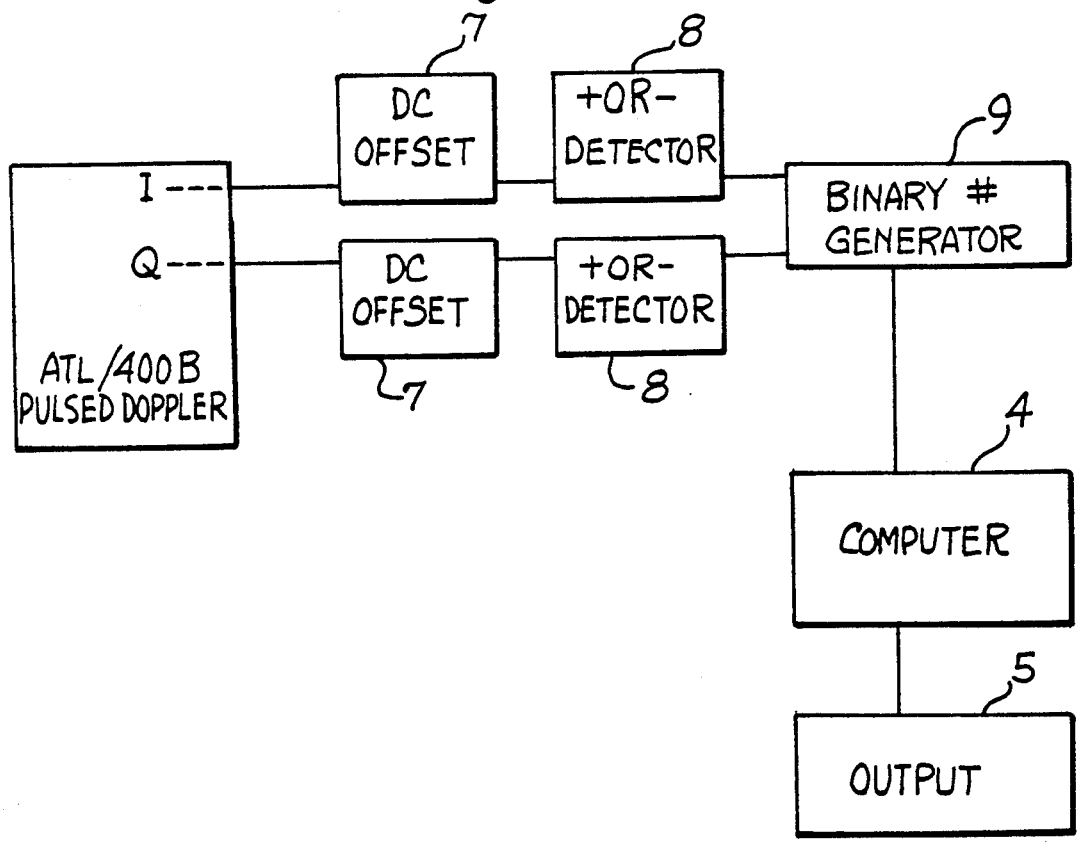
FIG. 9 (on the drawing sheet with FIG. 3) is a very diagrammatic block circuit diagram of a medical ultrasonic diagnostic device in accordance with the present invention.

In summary, with reference to FIG. 9, the I and Q quadrature signals from the ATL/400B pulsed Doppler are shifted to remove the DC component, as indicated by boxes 7, and detectors 8 in combination with a binary number generator circuit 9 characterize the phase of the echo signal in 90-degree increments by means of a two-digit binary number. The computer 4 stores the "last line" and "this line" data and computes the amount of displacement at the indicated depth. At the next sampling, the previous "last line" data is replaced by the previous "this line" data. Updated "this line" data is used to calculate the next displacement.

Figure 10:
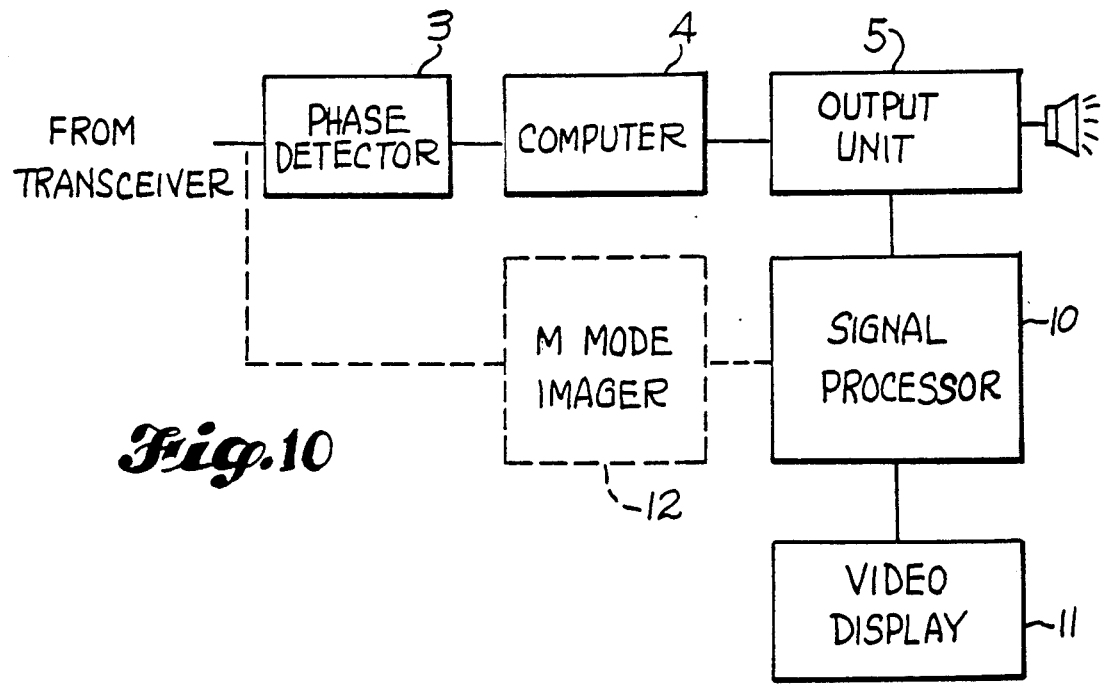
FIG. 10 and FIG. 11 are very diagrammatic block circuit diagrams of modified devices in accordance with the present invention.

The very precise determination of tissue displacement at discrete but closely adjacent depths makes possible new noninvasive diagnostic ultrasonic medical devices. One such new instrument allows detection of amplified audio frequency vibrations occurring in tissue inside the body. The beating of the heart, for example, induces audible frequency vibrations of internal tissue, some of which can be heard at the surface by use of a stethoscope. With reference to FIG. 10, the computer 4 calculating the small, rapidly occurring displacements of internal tissue can be programmed to concentrate on a depth of interest and detect displacement oscillations or pulsations (echo phase reversals) occurring at such depth at a frequency in the audible frequency range.

The computer can actuate an output unit 5 to generate a corresponding audio output at the detected frequency. Amplitude can be indicated by volume. The overall effect of such device is similar to placing the sensing end of a conventional stethoscope inside the body where sounds can be "heard" which otherwise would be muted in transmission to the surface or which may be drowned out by background or other noises. In a specialized application, the depth (range gate) of interest can be selected to overlap fetal tissue pulsating due to pounding of the fetal heart so that the output would consist primarily of fetal heart tones which can be difficult to hear by use of a conventional stethoscope.

In a modified device, the computer 4 can be programmed to calculate the frequency spectrum or a separate frequency spectrum analyzer 10 can be used for the audio frequency output. The frequency spectrum analyzer 10 can trigger a video display unit 11. Such display unit can indicate the dominant frequency of tissue vibrations sensed as a function of time. Such information could be useful to analyze development of the fetal heart, for example.

As indicated in broken lines in FIG. 10, in a related device the signal from the ultrasound transceiver can be fed to a substantially conventional M mode imaging unit to provide a familiar video output display shown in FIG. 3 is. There are known M mode units which generate or accept audible frequency Doppler information to colorize the display differently depending on the velocity detected at different depths. In accordance with the present invention, rather than colorizing the M mode display as a function of velocity, the output of the frequency spectrum analyzer 10 can be fed to the M mode imaging unit to colorize the M mode display depending on the audible frequency vibrations detected in tissue displacement. The depth of detection of the audio frequency displacement would be indicated in the M mode display, colored differently for different frequency ranges.

Figure 11:
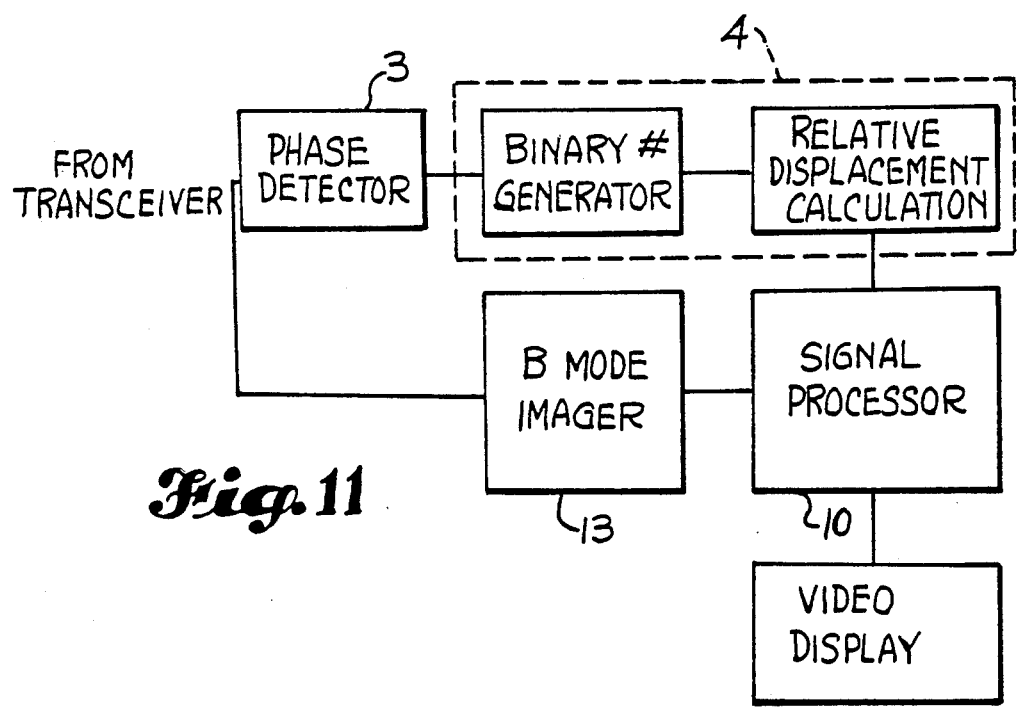

With reference to FIG. 11, in a modified system, the computer 4 can be programmed to detect, calculate and quantify other characteristics of the underlying tissue or matter being scanned. For an "ultrasonic plethysmograph" the computer 4 is programmed not only to quantify the displacement of tissue at different depths, but also to compare the displacement occurring at different depths and quantify the relative expansion or contraction of tissue. Because of the multiplicity of range gates, plethysmography information from a desired depth can be obtained. Prior plethysmographs may allow approximate evaluation of gross volume changes such as the cross-sectional size of an entire limb or evaluation of surface changes such as fluctuations in translucency due to pulsing of blood through the tissue. By use of the present invention, the phase detector allows computation of small displacements at different depths which can be compared to reveal expansion and contraction of a section of tissue deep beneath the skin.

The frequency of pulsation of the tissue can be calculated at any desired depth of interest, as well as the amplitude of pulsation. Evaluation may reveal or rule out irregular blood supply to the region. Similarly, at a desired depth of interest the time delay from the beginning of the cardiac R wave to expansion of underlying tissue representing the surge in blood supply may be useful for detecting irregularities. As for the ultrasonic stethoscope discussed above, the frequency spectrum of tissue expansion and contraction can be calculated and displayed by use of a frequency spectrum analyzer 10. In a more sophisticated instrument, a two-dimensional B mode imager 13 can be fed the frequency spectrum information to colorize the two-dimensional, cross-sectional display and provide new information or make it easier to interpret. For example, one popular use for B mode imaging systems is to display representations of a fetus inside the uterus. The present invention can detect pulsations of tissue indicative of tissue supplied by the maternal heart which, at rest, would be beating at less than 100 beats per minute and colorize those portions of the B mode image. Where expansion and contraction of tissue at a frequency much higher than 100 beats per minute is detected, the corresponding portions of the B-mode image can be colorized differently to indicate tissue supplied by the fetal heart.

Apart from colorization of B mode images, the information on tissue expansion and contraction can be useful for medical diagnosis. Tissues detected to have a delayed expansion (compared to the normal delay from a cardiac R wave, for example) may indicate plugged blood supply vessels, and tissues having accentuated expansion amplitude in a suspect area, such as the breast, may indicate irregular increased blood supply to a specific area such as a tumor.

We claim:

1. The method of quantifying relative displacement of internal body matter at different depths below the skin which method comprises transmitting a first burst of ultrasound into the body from the skin, measuring the phase of ultrasound of the first burst reflected from internal body matter a first predetermined period after transmission of the first burst, measuring the phase of ultrasound reflected by internal body matter a second predetermined period after transmission of said first burst, subsequently transmitting a second burst of ultrasound into the body, measuring the phase of ultrasound of the second burst reflected from internal body matter a predetermined period of the same duration as the first predetermined period after transmission of the second burst, measuring the phase of the ultrasound of the second burst reflected from an internal body matter a predetermined period of the same duration as the second predetermined period after transmission of the second burst, and comparing the change in measured phases of the reflected ultrasound to determine the relative displacements of body matter at the different depths corresponding to the length of time required for ultrasound to travel to and return from body matter during the first and second predetermined periods.

2. The method of determining and registering variations of expansion and contraction of body tissue by blood passing through the tissue which comprises scanning such tissue with a pulped Doppler medical instrument by transmitting waves toward such tissue and detecting and analyzing echoes of such waves, measuring displacement of such tissue at a plurality of depths of interest by measurement of phase change of the echoes, comparing such displacements at different depths so as to detect relative expansion and contraction of the tissue, and providing an output indicative of expansion and contraction of such tissue.

3. The method defined in claim 2 including providing an output of the frequency of expansion and contraction of the tissue.

4. The method defined in claim 2 including providing an output of the amplitude of expansion and contraction of the tissue.

5. The method defined in claim 2 including measuring the time delay from the beginning of a cardiac signal to the beginning of expansion of the tissue signifying a surge in blood supply through the tissue.

6. The method defined in claim 2 including providing an output of the frequency spectrum of expansion and contraction of the tissue.

7. The method defined in claim 2, including generating a video display of an image of the tissue and colorizing the display based on the output indicative of tissue expansion and contraction.

8. The method of quantifying expansion and contraction of internal body tissue in a region below the skin to evaluate blood supply to the tissue which method comprises transmitting a first burst of ultrasound into the body from the skin, measuring the phase of ultrasound of the first burst reflected from internal body matter a first predetermined period after transmission of the first burst, measuring the phase of ultrasound reflected by internal body matter a second predetermined period after transmission of said first burst, subsequently transmitting a second burst of ultrasound into the body, measuring the phase of ultrasound of the second burst reflected from internal body matter a predetermined period of the same duration as the first predetermined period after transmission of the second burst, measuring the phase of the ultrasound of the second burst reflected from internal body matter a predetermined period of the same duration as the second predetermined period after transmission of the second burst, and comparing the change in measured phases of the reflected ultrasound to determine the expansion and contraction of body tissue in the region at a depth corresponding to the length of time required for ultrasound to travel to and return from body matter during the first and second predetermined periods.

9. The method of determining and registering variations of expansion and contraction of internal body tissue to evaluate blood supply to tissue which comprises scanning such tissue with a pulsed Doppler medical instrument by transmitting waves toward such tissue and detecting and analyzing echoes of such waves, measuring displacement of such tissue at a plurality of depths of interest by measurement of phase change of the echoes, comparing such displacements at different depths so as to detect relative expansion and contraction of the tissue, and providing an output indicative of expansion and contraction of such tissue.

10. The method defined in claim 9, including providing an output of the frequency of expansion and contraction of the tissue.

11. The method defined in claim 9, including providing an output of the amplitude of expansion and contraction of the tissue.

12. The method defined in claim 9, including measuring the time delay from the beginning of a cardiac signal to the beginning of expansion of the tissue signifying a surge in blood supply through the tissue.

13. The method defined in claim 9, including providing an output of the frequency spectrum of expansion and contraction of the tissue.

14. The method defined in claim 9, including generating a video display of an image of the tissue and colorizing the display based on the output indicative of tissue expansion and contraction.

* * * * *

UNITED STATES PATENT AND TRADEMARK OFFICE
CERTIFICATE OF CORRECTION

PATENT NO. : 5,183,046                      Page 1 of 2

DATED : February 2, 1993

INVENTOR(S) : K. W. Beach et al.

It is certified that error appears in the above-identified patent and that said Letters Patent is hereby corrected as shown below:

| COLUMN | LINE | |
|---|---|---|
| 1 | 21-23 | after "fre-quency" delete "of reflected waves as compared to the fre-quency" |
| 3 | 16-20 | after "ultrasound." delete "to the devices measuring frequency shift, the phase signal is analyzed mathematically by integration to approximate displacement of tissue. Consequently, errors can be introduced both in phase measurement and" |
| 3 | 41 & 42 | after "ultra-sonic" insert --Doppler medical device, the echo of such pulse reflected-- |
| 3 | 43 | after "sampling" insert --such-- |
| 4 | 53 | "provided" should read --provides-- |
| 5 | 9 | "tat" should read --that-- |

UNITED STATES PATENT AND TRADEMARK OFFICE
CERTIFICATE OF CORRECTION

PATENT NO. : 5,183,046
DATED : February 2, 1993
INVENTOR(S) : K. W. Beach et al.

It is certified that error appears in the above-identified patent and that said Letters Patent is hereby corrected as shown below:

| COLUMN | LINE | |
|---|---|---|
| 7 (Claim 1 | 44 Line 16) | after "from" delete "an" |
| 7 (Claim 2 | 56 Line 4) | "pulped" should read --pulsed-- |
| 8 (Claim 9 | 41 Line 3) | after "supply to" insert --the-- |

Signed and Sealed this

Eleventh Day of January, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,183,046

DATED : February 2, 1993

INVENTOR(S) : K. W. Beach et al.

Page 1 of 2

It is certified that error appears in the above-identified patent and that said Letters Patent is hereby corrected as shown below:

| COLUMN | LINE | |
|---|---|---|
| 1 | 21-23 | after "fre-quency" delete "of reflected waves as compared to the fre-quency" |
| 3 | 16-20 | after "ultrasound." delete "to the devices measuring frequency shift, the phase signal is analyzed mathematically by integration to approximate displacement of tissue. Consequently, errors can be introduced both in phase measurement and" |
| 3 | 41 & 42 | after "ultra-sonic" insert --Doppler medical device, the echo of such pulse reflected-- |
| 3 | 43 | after "sampling" insert --such-- |
| 4 | 53 | "provided" should read --provides-- |
| 5 | 9 | "tat" should read --that-- |

UNITED STATES PATENT AND TRADEMARK OFFICE
CERTIFICATE OF CORRECTION

PATENT NO. : 5,183,046
DATED : February 2, 1993
INVENTOR(S) : K. W. Beach et al.

It is certified that error appears in the above-identified patent and that said Letters Patent is hereby corrected as shown below:

| COLUMN | LINE | |
|---|---|---|
| 6 | 26 & 27 | after "output" delete "display shown in FIG. 3 is" |
| 7 (Claim 1 | 44 Line 16) | after "from" delete "an" |
| 7 (Claim 2 | 56 Line 4) | "pulped" should read --pulsed-- |
| 8 (Claim 9 | 41 Line 3) | after "supply to" insert --the-- |

This certificate supersedes Certificate of Correction issued January 11, 1994

Signed and Sealed this

Tenth Day of May, 1994

Attest:

BRUCE LEHMAN

Attesting Officer

Commissioner of Patents and Trademarks